United States Patent [19]

Stone et al.

[11] Patent Number: 5,527,316
[45] Date of Patent: Jun. 18, 1996

[54] SURGICAL REAMER

[76] Inventors: Kevin T. Stone, 2940 E. Patterson Rd.; Daniel E. Williamson, 895 S. Caleb Ct.; Jane A. Sheetz, 3968 W. Crystal Lake Rd., all of Warsaw, Ind. 46580

[21] Appl. No.: 200,199

[22] Filed: Feb. 23, 1994

[51] Int. Cl.$^6$ ................................. A61B 17/56
[52] U.S. Cl. ............... 606/80; 606/89; 606/96; 623/23; 408/127
[58] Field of Search ............... 606/80, 89, 87, 606/96, 180, 81, 84, 85; 623/23, 22; 408/230, 127, 204

[56] References Cited

U.S. PATENT DOCUMENTS

| | | | |
|---|---|---|---|
| 4,127,355 | 11/1978 | Oakes | 408/225 |
| 4,285,618 | 8/1981 | Shanley, Jr. | 408/230 X |
| 4,536,107 | 8/1985 | Sandy et al. | 408/230 X |
| 4,706,659 | 11/1987 | Matthews et al. | |
| 4,751,922 | 6/1988 | DiPietropolo | 606/80 X |
| 5,017,057 | 5/1991 | Kryger | 408/127 X |
| 5,089,004 | 2/1992 | Averill et al. | 606/85 |
| 5,342,363 | 8/1994 | Richelsoph | 606/79 |
| 5,387,218 | 2/1995 | Meswania | 606/80 |
| 5,403,320 | 4/1995 | Luman et al. | 606/89 |

FOREIGN PATENT DOCUMENTS

| | | | |
|---|---|---|---|
| 2542056 | 3/1977 | Germany | 606/80 |

OTHER PUBLICATIONS

Excerpts from 1978 HOWMEDICA Catalog (three pages) "For that Extra Margin of Interface Integrity : The New Howmedica Intramedullary Brush", author unknown.

*Primary Examiner*—Stephen C. Pellegrino
*Assistant Examiner*—Guy V. Tucker
*Attorney, Agent, or Firm*—Harness, Dickey & Pierce

[57] ABSTRACT

A surgical reamer is used in conjunction with a femoral neck cutting guide to enlarge the intramedullary canal of a resected host femur to expose hard cortical bone. The reamer has a longitudinally fluted cutting head that is flexible and able to bend relative to its longitudinal axis whereby to conform to axial or curved cortical bone surfaces to be engaged by like mating surfaces of a hip prosthesis to be implanted therein. In this regard, the cutting head includes a helical band spiralling between the ends of the cutting head.

24 Claims, 6 Drawing Sheets

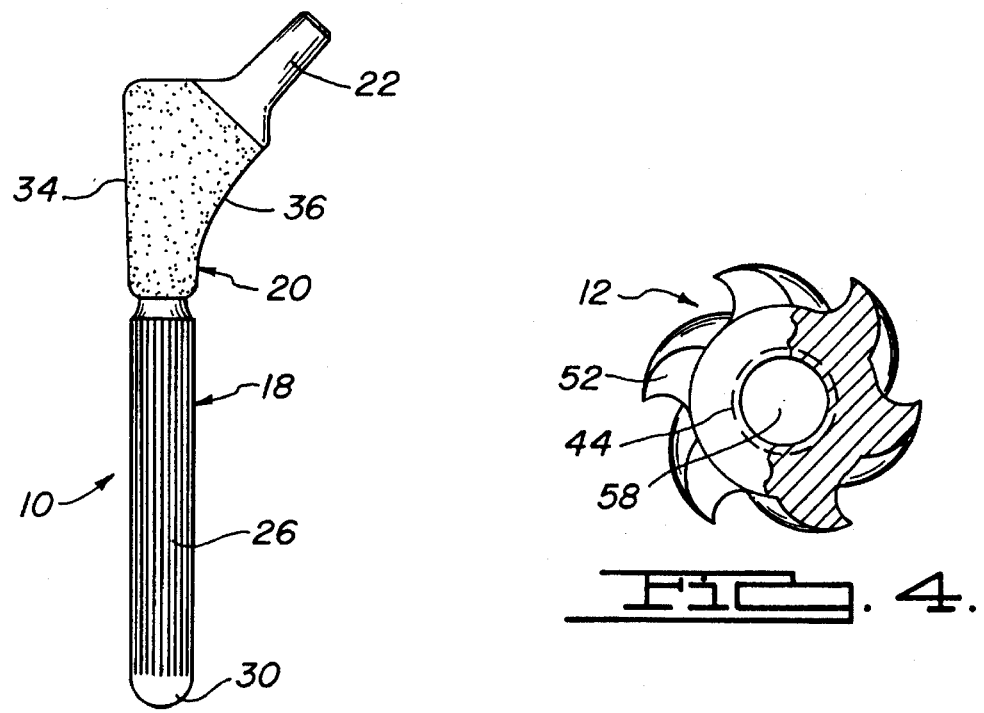
FIG. 1.
FIG. 4.
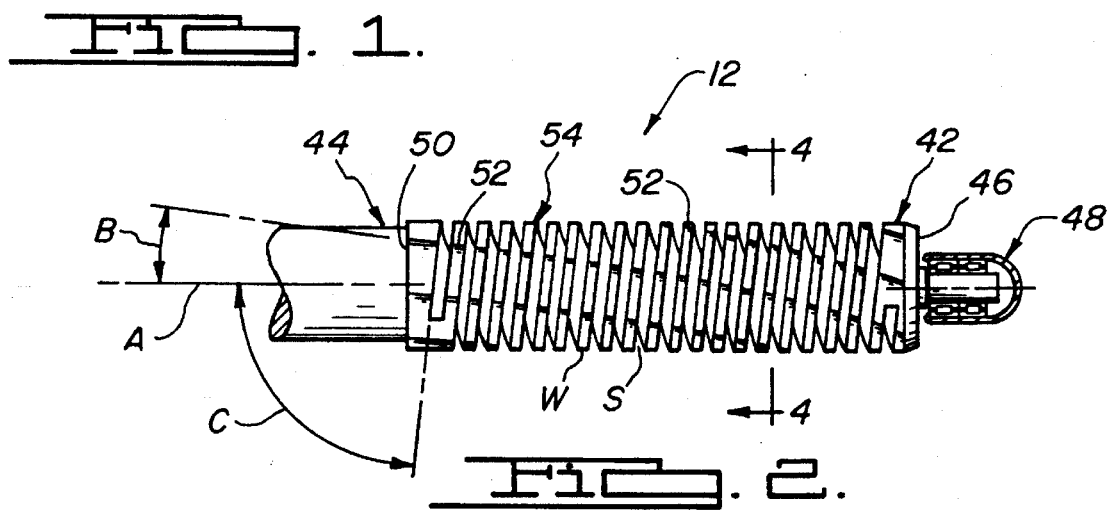
FIG. 2.
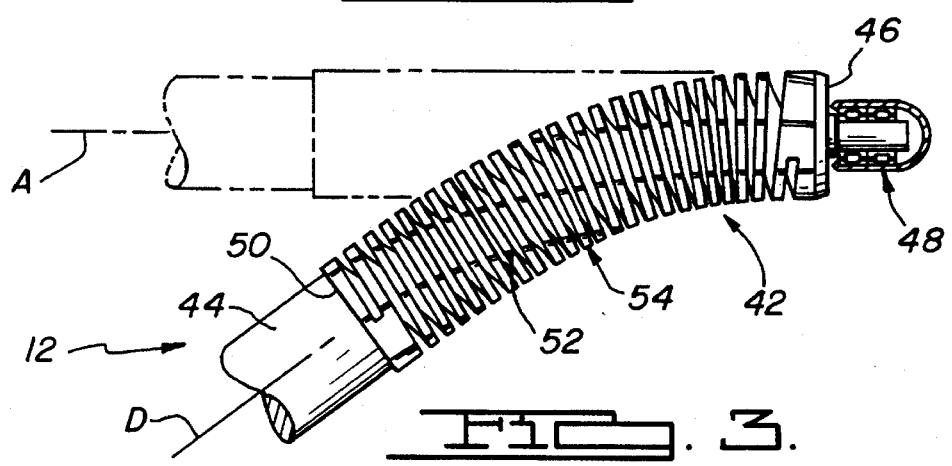
FIG. 3.

SURGICAL REAMER

BACKGROUND OF THE INVENTION

This invention relates generally to a method of and surgical apparatus for use in preparing a bone cavity for subsequent implantation of a joint replacement prosthesis. The invention has particular application to a surgical reamer for enlarging and shaping a cavity within a femur for the implantation of the femoral component of a hip joint prosthesis.

A natural hip joint may undergo degenerative changes due to a variety of etiologies. When these changes become so far advanced and irreversible, it may become necessary to replace the natural hip joint with a prosthetic hip. When implantation of such a hip prosthesis becomes necessary, the head of the natural femur is resected and a cavity is created within the intramedullary canal of the host femur for accepting and supporting the prosthetic hip.

Conventionally, the cavity within the intramedullary canal is formed in part by using a series of rasps, each of which comprises a handle and a serrated shank joined to the handle. To form the cavity, each of the rasps are in turn moved sequentially into and out of the cavity in generally a straight line. However, such a movement may not produce the ideal cutting action when the surface to be formed is curved to follow the medial cortex, and sometimes the anterior, posterior and lateral cortices. Reamers have also been used to form cavities in the intramedullary canal prior to the implantation of a hip joint prosthetic device. However, such reamers were generally inflexible and therefore do not precisely follow the shape of the cortical bone.

SUMMARY OF THE INVENTION

The present invention provides a surgical reamer for enlarging a cavity within a bone, as well as a method for forming a cavity within a bone. The surgical reamer comprises a cutting head extending along a section of the length of a shank, and a plurality of generally helical flutes extending radially outwardly of the cutting head for reaming the bone, the flutes extending longitudinally at least partially between the leading and trailing ends of the cutting head. The cutting head is formed as a continuous helical band which spirals about the longitudinal axis and at least partially between the leading and the trailing ends of the cutting head, the band describing a coil-like body which enables the cutting head to flex and curve relative to its axis during rotation of the shank so as to allow the cutting head to conform to the curvature of the cortex.

A method of forming the surgical reamer includes centrally boring the interior of a longitudinally fluted cylindrical cutting head and cutting a helix through the wall of the head to form a continuous helical band which spirals between the ends of the head. The helical band allows the cutting head to undergo axial changes and enables the cutting head to flex and bend relative to its longitudinal axis. The method of forming a cavity within the femur includes reaming a resected portion of the bone to form a cavity of a diameter generally greater than that of the cutting head, potentially positioning a cutting guide relative to the resected portion, and positioning a shaft of the reamer relative to the cutting guide. The cutting head is rotated within the cavity while the shaft is being manipulated to enlarge the cavity.

An advantage of the present invention is to provide a method and apparatus for implanting a prosthetic device that includes a flexible reamer which enables a prosthetic device to be placed accurately against the hard cortex of the bone.

Another advantage of the present invention is to provide a method and apparatus for implanting a prosthetic device that allows a cavity to be formed in bone, the shape of which follows the natural curved hard cortex portion of the bone.

A further advantage of the present invention is to provide a method and apparatus for implanting a prosthetic device that is relatively easy to use and provides for repeatability when used in the same manner. A related advantage of the invention is to provide a method and apparatus for implanting a prosthetic device that is relatively simple and relatively inexpensive to manufacture.

BRIEF DESCRIPTION OF THE DRAWINGS

Additional advantages and features of the present invention will become apparent from the following description and appended claims, taken in conjunction with the accompanying drawings in which:

FIG. 1 is an elevational view of a conventional modular hip prosthesis which may be implanted according to the teachings of a preferred embodiment of the present invention;

FIG. 2 is a side elevational view of a surgical reamer having a flexible cutting head according to the teachings of a preferred embodiment of the present invention;

FIG. 3 is a side elevational view of the surgical reamer shown in FIG. 2 undergoing flexure relative to the longitudinal axis of the shank according to the preferred embodiment of the present invention;

FIG. 4 is a partial sectional view of the cutting head of the surgical reamer taken along line 4—4 of FIG. 2 according to the teachings of a preferred embodiment of the present invention;

DETAILED DESCRIPTION OF THE PREFERRED EMBODIMENTS

Figure 5:
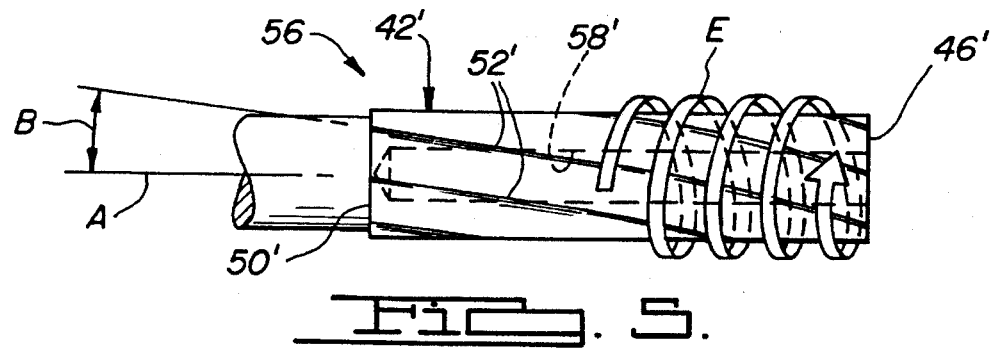
FIG. 5 illustrates the method by which the surgical reamer is formed according to the teachings of a preferred embodiment of the present invention

It should be understood that while this invention is described in connection with a particular example, the scope of the invention need not be so limited. Rather, those skilled in the art will appreciate that the following teachings can be used in much wider variation of applications than the example specifically mentioned herein.

Referring now to the drawings, FIGS. 1–17 illustrate a preferred embodiment of the present invention, including a modular hip prosthesis 10 used to replace a natural hip after the natural hip has degenerated, a specially configured surgical reamer 12 for enlarging a cavity formed within a host femur 14 to receive the hip prosthesis 10, and surgical apparatus including a proximal reaming guide 16. As shown in FIG. 1, the hip prosthesis 10 includes a distal segment 18, a proximal segment 20 and a tapered stem 22 which is adapted to receive the head portion of the hip prosthesis 10. As used herein, the distal and proximal segments 18 and 20 are provided in different sizes and with different anterior, posterior and medial surfaces depending on the host femur 14.

The distal segment 18 is an elongated cylindrical member that is inserted into a specially reamed diaphyseal cavity 24 in the host femur 14 and is used to provide stability for the hip prosthesis 10. The distal segment 18 comprises a fluted stem portion 26 which engages the wall 28 of the diaphyseal cavity 24 and a rounded lower end portion 30. The proximal segment 20 is operable to be implanted in a metaphyseal cavity 32 formed in the host femur 14 and includes a longitudinal portion 34 and a blended medial construct portion 36, the segment portions 34 and 36 being specially configured and adapted to seat against the hard cortical bone 38 and 40 of the metaphyseal cavity 32, respectively. By configuring the medial construct portion 36 in this manner, much of the force transferred by the hip prosthesis 10 to the host femur 14 is absorbed by the cortical bone 40. This increases the rotational stability of the hip prosthesis 10 and provides for the physiological transfer of load along the trabecular path.

The surgical reamer 12 which is used during implantation of the modular hip prosthesis 10 will now be described with reference to FIGS. 2–4. The surgical reamer 12 comprises a flexible generally cylindrical cutting head 42 and an elongated axial drive shaft 44 for driving the cutting head 42. The cutting head 42 and the elongated axial drive shaft 44 are each generally coaxially arranged relative to a central longitudinal axis of rotation designated by the letter "A". The cutting head 42 has a leading end 46 provided with an alignment bearing 48 to seat the cutting head 42 within the proximal reaming guide 16 in a manner to be more fully described below. In addition, the cutting head 42 has a trailing end 50 from which the drive shaft 44 extends, and a plurality of cutting teeth 52 that extend radially outwardly from the head 42. The cutting teeth 52 are generally helical and spiral longitudinally along the length of and between the ends 46 and 50 of the cutting head 42. The cutting teeth 52 act to cut material from the bone and are arranged to form grooves which remove of the material cut from the bone.

To enable the surgical reamer 12 to accurately form to the cortical bone 38 and 40, the cutting head 42 is centrally hollow 58 and constituted in part as a continuous helical band 54 that spirals about the longitudinal axis "A" and extends, at least in part, between the ends 46 and 50 of the cutting head 42. The helical band 54 enables the cutting head 42 to deflect and flex relative the axis "A" during rotation of the drive shaft 44, thereby allowing the cutting head to motionly enlarge the metaphyseal cavity 32 but also to accurately form the surfaces 38 and 40 for the hip prosthesis 10. The helical band 54 is generally uniform in width and spacing, indicated respectively as "W" and "S", and rectangular in cross-section The long dimension of the cross-section being disposed on a radius passing through the longitudinal axis "A" and the short dimension of the cross-section being disposed on a line that is generally parallel to the longitudinal axis "A". The radial thickness of the helical band 54 determines the mass and area moments of inertia of the cutting head 42 and the helical gap formed by the spiralling band determines the flexibility of the cutting head 42. In addition, both the radial thickness and the helical gap of the helical band 54 determine the resistance of the cutting head 42 to torque.

The number of cutting teeth 52 and the helix angle of the cutting teeth will depend on the particular application, such as the density of the material being reamed. In the embodiment shown, the cutting head 42 includes six cutting teeth 52 that are generally helical and extend generally spiral radially about the longitudinal axis of the cutting head 42. The helix angle of successive cutting teeth 52, generally designated by the letter "B", is between 0°–45° with respect to the longitudinal axis Preferably, the helix angle "B" is about 15°. Further, the helical band 54 is formed by a helix angle, generally designated by the letter "C", of about 60°–89° to the longitudinal axis Preferably the helix angle "C" is about 84°.

The direction of rotation of the drive shaft 44, the sense of the helix angle "B" of cutting teeth 52, and the sense of the helix angle "C" of helical band 54 are preferably opposite. This allows the exterior contour of the cutting head 42 to collapse radially if the cutting teeth 52 bit too much during a reaming operation thereby ensuring that excess bone material is not removed. In some applications, the helical sense of the helical band 54 and the cutting teeth 52 could be the same as one another.

As shown in FIG. 5, the surgical reamer 12 can conveniently be manufactured from a conventional reamer 56 that includes a solid cylindrical cutting head 42' and a plurality of flutes (i.e., cutting teeth) 52'. The cutting head 42' is centrally bored at 58' from the leading end 46' axially inwardly towards the trailing end 50' thereby forming a centrally hollow member, (i.e., entire cutting head could be hollow). Thereafter, as shown by the spiral "E", a helix of specified width and spacing is cut through the wall of the cutting head 42' to thereby form the continuous helical band 54. Although the bore 58' is shown as being generally cylindrical and the wall of the cutting head 48' is shown as being generally cylindrical and of uniform thickness, the bore wall could be frusto-conical or shaped as desired to effect the flexural properties desired of the cutting head 42. Additionally, the width and thickness of the band and the forming helix could vary as each extends between the ends of the head.

Figure 7:
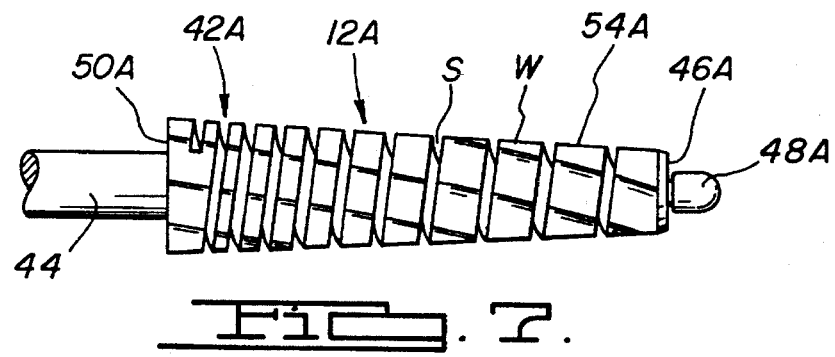
Figure 8:
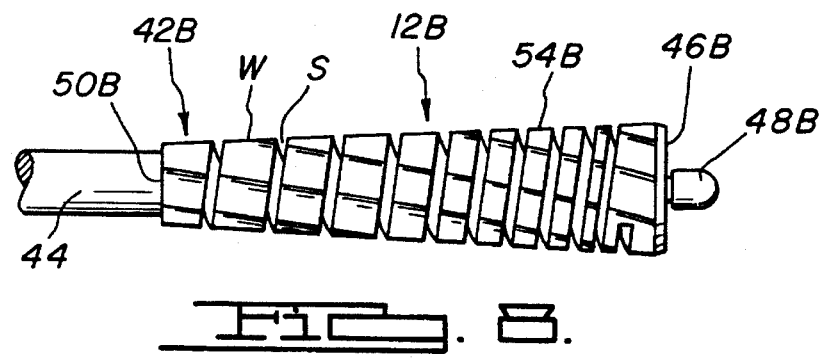
FIG. 8 is a section view showing a bearing support formed at the end of the cutting head according to the preferred embodiments of the present invention.

Alternative embodiments of the cutting head 42 are shown in FIGS. 7 and 8. In this regard, the cutting head 42A has a "positive" taper and the cutting head 42B has a "negative" taper, each cutting head being constructed as a continuous helical coil or band 54A and 54B that spirals between the opposite axial ends of the respective head. Preferably, for the frusto-conical cutting head 42A, the longitudinal width of the helical band 54A adjacent to the leading end 46A (smaller diameter) is greater than the width of the band adjacent to the trailing end 50A where the cutting head has a greater diameter. To produce a constant radius, uniform flexibility is achieved by varying the width of the band in conjunction with the diameter of the band as described above. Conversely, for the frustoconical cutting head 42B, the longitudinal width of the helical band 54B adjacent to the leading end 46B (larger diameter) is less than the width of the band adjacent to the trailing end 50B where the cutting head has a smaller diameter. In either of the cutting heads 42A and 42B, the helical separation could be uniform or vary between the ends of the helical path.

Figure 6:
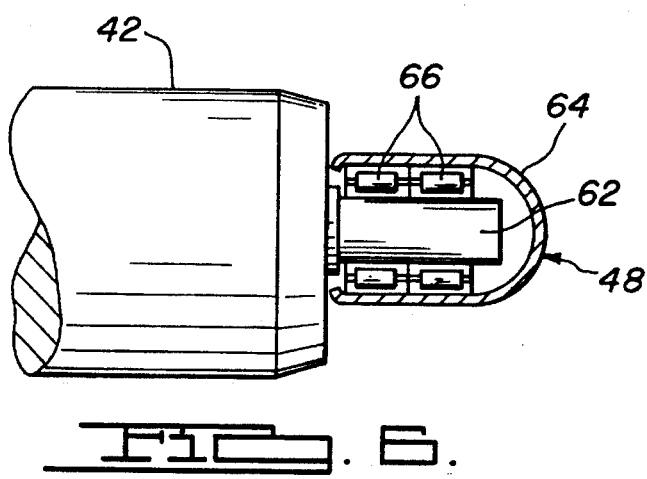
FIGS. 6 and 7 are side elevational views of a surgical reamer having a flexible cutting head according to the teachings of alternative preferred embodiments of the present invention.

The alignment bearing 48 will now be described in greater detail as shown in FIG. 6. The alignment bearing 48 mounted to the leading end 46 allows the cutting head 42 to be constrained in a shaped guide cavity 60 and rotate relative to the proximal reaming guide 16. The alignment bearing 48 includes a bearing shaft 62 that extends from the end face 46, a cup-shaped bearing housing 64, and one or more sets of bearings 66 mounted inside the housing. The bearing housing 64 is upwardly open to receive the bearing shaft.

Figure 9A:
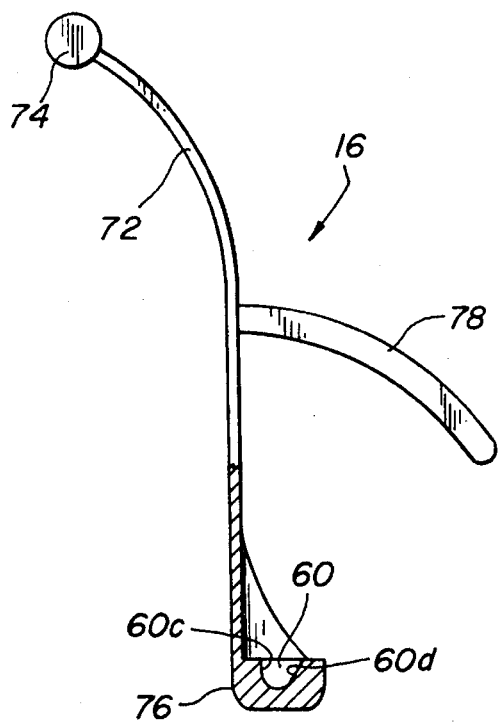
FIGS. 9A and 9B are side and front elevational views of a proximal reaming guide according to the teachings of a preferred embodiment of the present invention.
Figure 9B:
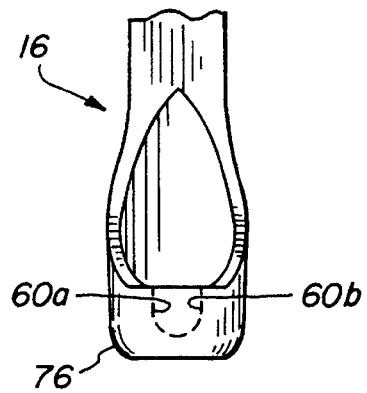
Figure 10A:
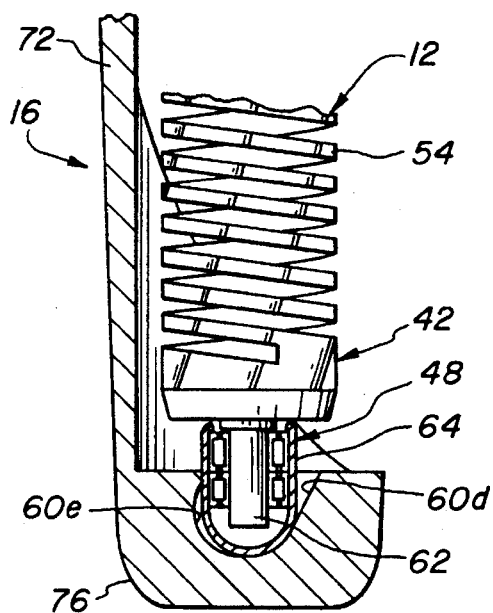
FIGS. 10A and 10B are side elevational views, partially in section, of the cutting head positioned in the proximal reaming guide according to the teachings of the preferred embodiments of the present invention.
Figure 10B:
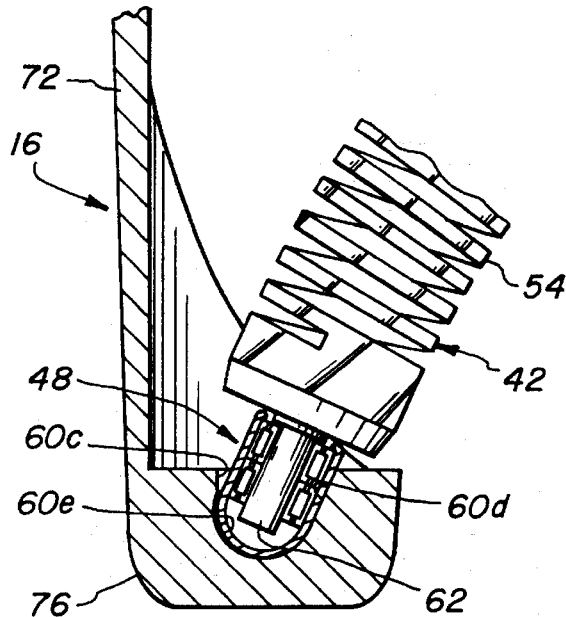
Figure 11A:
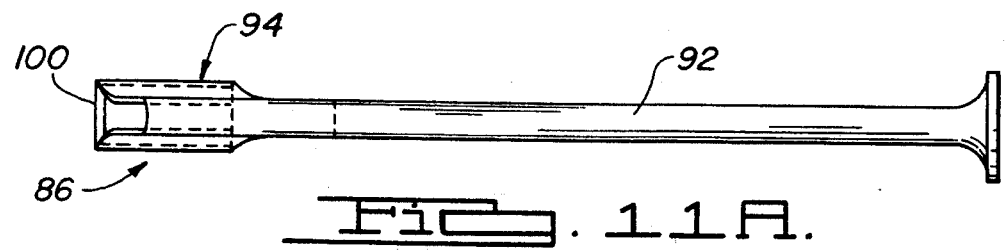
FIGS. 11(A)—11(C) are side and end views of a chisel for use with the preferred embodiments of this invention.
Figure 11B:
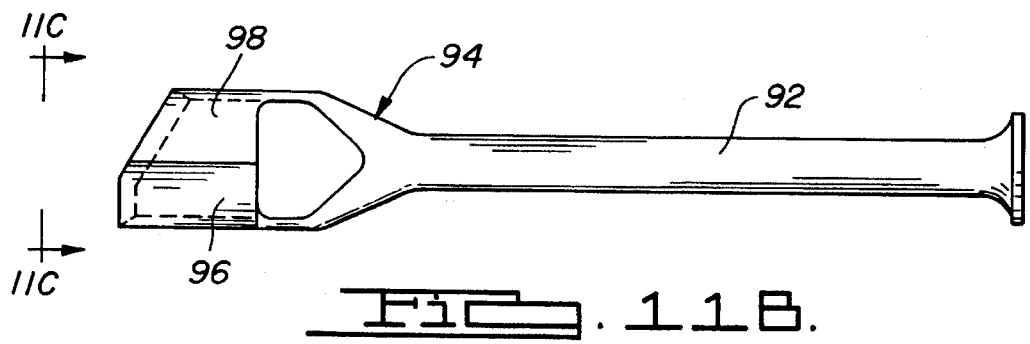
Figure 11C:
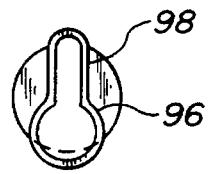
Figure 12:
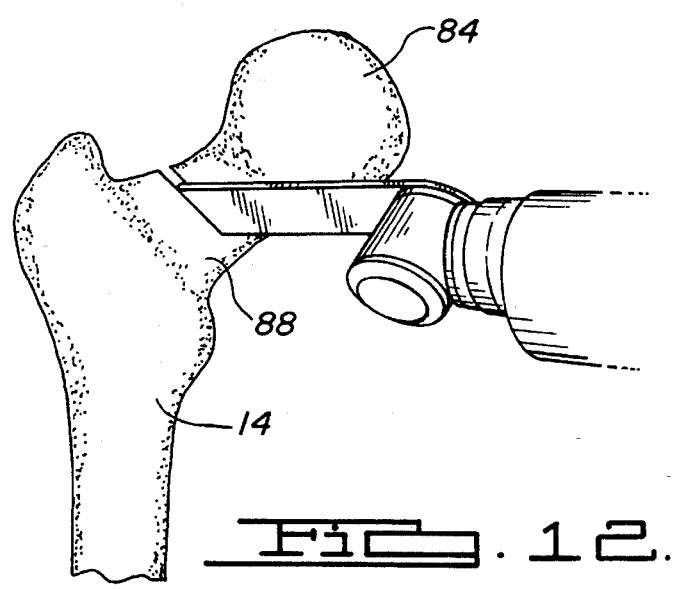
FIGS. 12—15 illustrate some of the steps in the method of preparing a femur for the hip prosthesis according to the teachings of the preferred embodiments of the present invention.
Figure 13:
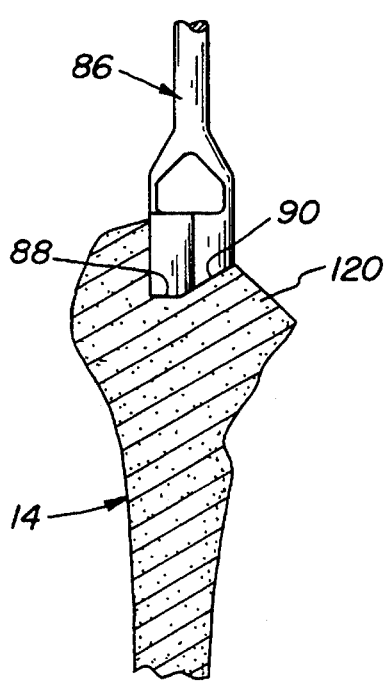
Figure 14:
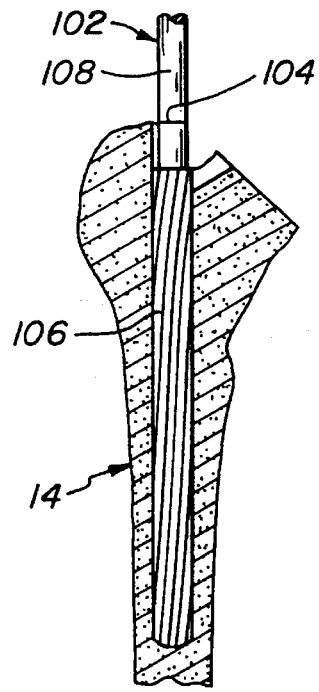
Figure 15:
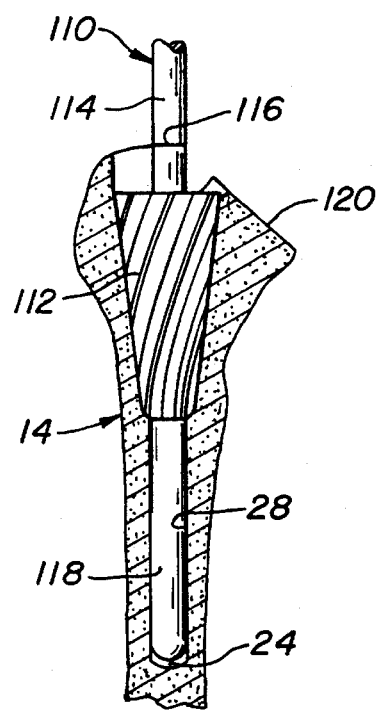

The proximal reaming guide 16 will now be described with reference to FIGS. 9A and 9B. The proximal reaming guide 16 includes a curved guide body 72 having an upper handle 74 and a lower guide base 76, and a guide arm 78 extending from the curved guide body 72. The lower portion of the guide body 72 is mounted in the femoral cavity and configured to abut the cortical bone 38, at least in part, and position the guide arm 78 relative to the cortical bone 40. The lower base 76 seats at the bottom of the metaphyseal cavity 32 and is provided with the shaped guide cavity 60 to receive and support the alignment bearing 48. The alignment guide arm 78 and the guide cavity 60 cooperate to position and guide the surgical reamer 12 in the metaphyseal cavity 32. The guide arm 78 is generally elliptically shaped and engages the drive shaft 44 to constrain the movement of the cutting head 42 relative to the metaphyseal cavity 32.

According to an important feature of this invention, the guide cavity 60 is configured to generally vertically align the longitudinal axis of the cutting head 42 relative to a vertical axis through the proximal reaming guide 16 and control the onset of flexure of the cutting head 42. As shown, the guide cavity 60 is generally vertically disposed and includes a lateral side wall 60c and a medial side wall 60d, a posterior end wall 60b and an anterior end wall 60a. The end walls 60a and 60b and the lateral side wall 60c provide a snug engagement with and inhibit any translational movement of the bearing housing 64 and cutting head 42. Should the drive shaft 44 be moved relative to the guide arm 78, the walls 60a and 60b can resist rotation and cause flexure of the cutting head. The lateral side wall 60c has a lower cavity 60e and the medial side wall 60d is at an angle to allow the cutting head and bearing housing to be rotated medially, each generally axially aligned. When the bearing housing 64 engages the sloped medial side wall 60d, the bearing housing 64 will seat in the lower cavity 60e and abut the medial wall and resist further medial movement causing the cutting head 42 to begin to undergo flexure.

In some applications, a generally cylindrically-shaped spool or guide sleeve 80 is located about the drive shaft 44 to inhibit axial compression of the helical band 54 and maintain a fixed distance between the guide arm 78 and the guide base 76. The guide sleeve 80 include a pair of annular lips 82 which engage the upper and lower faces of the guide arm 78 and constrain the guide sleeve 80 to orbit in a fixed radius about the host femur 14 while the cutting head 42 reams the neck portion of the femur 14. In some applications, the guide sleeve 80 remains rotationally stationary while the drive shaft 44 is rotated. In some applications, the guide sleeve 80 is not necessary because of the axial stiffness of the cutting head 42.

The method of the present invention will now be described with particular reference to FIGS. 11–16. After the hip is dislocated, the head 84 of the host femur 14 is resected. A chisel 86 is located on the superior surface 88 of the resected femur 14 and an axial force is applied to the chisel 86 to form a shaped cavity 90 in preparation for the hip prosthesis 10 and to establish a point of entry for a series of different reamers, as described below.

The chisel 86 includes an axially elongated handle 92 and a blade 94 having a key-hole shaped cross-section which emulates the outer surface configuration of the hip prosthesis 10. The blade 94 includes a cylindrical first blade portion 96 emulating the longitudinal portion 34 of the prosthesis and a U-shaped second blade portion 98 emulating the blended medial construct portion 36. The end faces of the first and second blade portions 96 and 98, respectively, are generally perpendicular to and disposed at an acute angle to the longitudinal axis of the handle 92. Preferably, the end face of the second blade portion 98 is disposed at about 60° to the longitudinal axis. Further, the end faces of the first and second blade portions 96 and 98, respectively, are formed to include a sharp V-shaped cutting edge 100. Preferably, the angle of the cutting edge 100 is about 30°.

After the chisel 86 forms the cavity 90, a series of reamers of different sizes are used in a sequential manner to form the diaphyseal and metaphyseal cavities 24 and 32 and expose the cortical bone. In this regard, a distal canal reamer 102 having a depth marking 104 is positioned in the cavity 90 and driven downwardly to ream the diaphyseal cavity 24. The distal canal reamer 102 includes a cylindrical head having a plurality of spiral or straight cutting flutes 106 and an upper shaft portion 108, the cutting flutes 106 being operable to pass debris from the diaphyseal cavity 24 during reaming. The depth marking 104 indicates to the surgeon when the diaphyseal cavity 24 has been reamed to the desired depth.

A metaphyseal reamer 110 is then used to remove an additional portion of the host femur 14 so as to begin formation of the metaphyseal cavity 32. The metaphyseal reamer 110 includes a fluted frusto-conical head 112, an upper drive shaft 114 having a depth marking 116, and a removable lower alignment shaft 118, the head 112 and the shafts 114 and 118 being generally coaxially disposed with the head 112 being disposed between the shafts 114 and 118. The metaphyseal reamer 110 is positioned above the metaphyseal cavity 32, the lower alignment shaft 118 is inserted into the diaphyseal cavity 24 so as to locate the metaphyseal reamer 110 with respect to the diaphyseal cavity 24 and the metaphysis 120 is reamed.

After the metaphysis 120 has been reamed, the neck portion 88 of the femur 14 is reamed so as to accommodate the medial construct portion 36 of the proximal segment 20. For this operation, the proximal reaming guide 16 is used with the alignment shaft 118. If desired, the alignment shaft 118 can be removably or integrally formed with the guide base 76.

Figure 16:
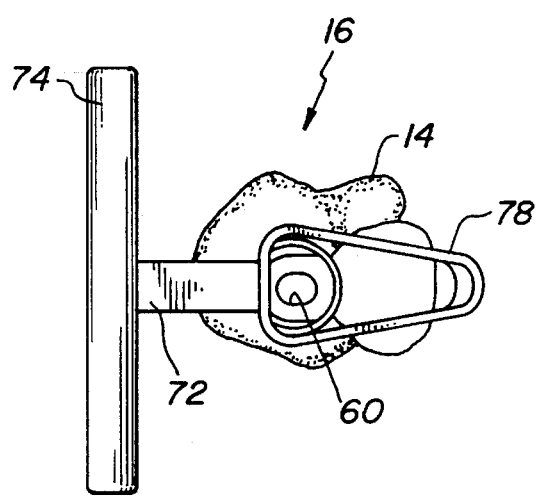
FIG. 16 is a top view showing the proximal reaming guide positioned in the femur according to the preferred embodiments of the present invention.
Figure 17:
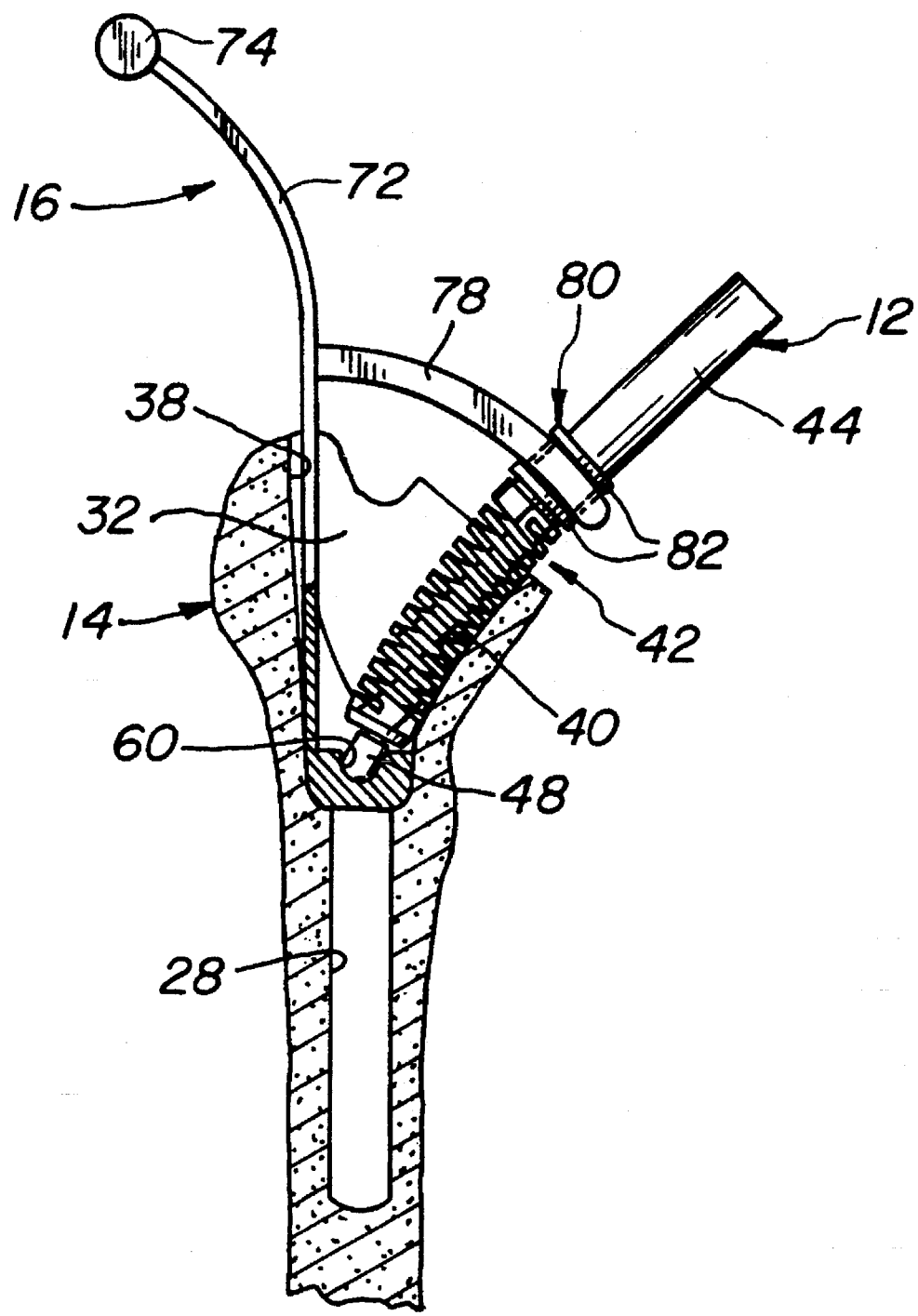
FIG. 17 is a side elevational view in section showing the method of enlarging a cavity within the femur for receiving the hip prosthesis according to the preferred embodiment of the present invention.

As can be seen in FIGS. 16 and 17, the proximal reaming guide 16 is mounted in the prepared cavity of the femur 14, and the guide arm 78 is positioned above the femur. The surgical reamer 12 is positioned within the proximal reaming guide 16 such that the alignment bearing 48 is seated within the cavity 60 of the guide base 76, the drive shaft 44 is located in the guide arm 78 with the guide sleeve 80 engaging the guide arm 78, and the cutting head 42 being constrained between the guide base 76 and the guide arm 78. The drive shaft 44 is then moved within the range of motion permitted by the guide arm 78. The presence of the helical band 54 enables the cutting head 42 to simultaneously rotate and flex along its length from the longitudinal axis "A" in a direction toward the axis "D" (see FIG. 3). During movement of the reamer 12, the cutting head 42 is allowed to orbit and flex to enlarge the metaphyseal cavity, remove cancellous bone material, and clean the cortical bone surface.

The metaphyseal cavity 32 is formed and inspected to ensure that the cortical bone has been exposed on the anterior interior surface of the host femur 14. The hip prosthesis 10 is then forced downwardly and into the cavity formed within the host femur 14.

The foregoing discussion discloses and describes merely exemplary embodiments of the present invention. The present invention may be used in forming cavities in different bone for use with other types of prosthetic joints such as knee joint prosthesis. One skilled in the art will readily recognize from such discussion, and from the accompanying drawings and claims, that various changes, modifications and variations can be made therein without departing from the spirit and scope of the invention.

What is claimed is:

1. A set of surgical instrumentalities for replacing a joint with a prosthetic joint, said set of surgical instrumentalities comprising:
   a prosthetic device; and
   a surgical reamer for preparing the joint to receive said prosthetic device, said surgical reamer including:
   (a) a cutting head with a longitudinal axis and opposing ends,
   (b) a helical band spiralling around said longitudinal axis and at least partially between said opposing ends of said cutting head, and
   (c) a cutting flute formed in said helical band, wherein said helical band allows said cutting head to flex with said opposed ends lying along relatively offset axes and allows said cutting head to remain along said relatively offset axes during rotation of said reamer.

2. The set of surgical instrumentalities for replacing a joint as set forth in claim 1, wherein said helical band defines a plurality of successive loops, the separation between said successive loops being generally uniform.

3. The set of surgical instrumentalities for replacing a joint as set forth in claim 1, wherein said helical band has a width that varies as said helical band extends between said opposing ends of said cutting head.

4. The set of surgical instrumentalities for replacing a joint as set forth in claim 1, wherein said helical band defines a plurality of successive loops, the separation between said successive loops varying between said opposing ends of said cutting head.

5. The set of surgical instrumentalities for replacing a joint as set forth in claim 1, wherein said helical band has a width and is defined in part by a plurality of successive loops, the width of said helical band and the separation between said plurality of successive loops being generally constant as the helical band extends between said opposing ends of said cutting head.

6. The set of surgical instrumentalities for replacing a joint as set forth in claim 1, wherein said cutting head includes a leading end and a trailing end, said surgical reamer further including an elongated shaft extending from said trailing end, said elongated shaft being operable to rotate said cutting head.

7. The set of surgical instrumentalities for replacing a joint as set forth in claim 6, wherein said cutting head is generally frusto-conical in shape with the diameter of said cutting head at said trailing end being greater than the diameter of said cutting head at said leading end.

8. The set of surgical instrumentalities for replacing a joint as set forth in claim 6, wherein said cutting head is generally frusto-conical in shape with the diameter of said cutting head at said trailing end being less than the diameter of said cutting head at said leading end.

9. The set of surgical instrumentalities for replacing a joint as set forth in claim 1, wherein said cutting head is generally cylindrical in shape and said helical band has a plurality of helical cutting flutes.

10. The set of surgical instrumentalities for replacing a joint as set forth in claim 9, wherein said cutting flutes extend generally longitudinally along a portion of said cutting head.

11. The set of surgical instrumentalities for replacing a joint as set forth in claim 9, wherein said cutting flutes spiral longitudinally along a portion of said cutting head.

12. The set of surgical instrumentalities for replacing a joint as set forth in claim 6, further comprising:
   a bearing shaft extending from said leading end of said cutting head; and
   bearing means for supporting said bearing shaft to permit rotation relative to said bearing shaft.

13. The set of surgical instrumentalities for replacing a joint as set forth in claim 12, wherein said bearing means comprises a bearing housing adapted to support said surgical reamer, and a roller bearing for allowing rotation of said bearing shaft with respect to said bearing housing.

14. A surgical reamer for enlarging a cavity within a bone to receive the prosthetic device, said surgical reamer including:
   (a) an elongated shaft having a longitudinal axis; and
   (b) a substantially hollow cylindrical cutting head disposed on said elongated shaft having opposed ends, said cutting head having at least one cutting flute and a helical band spiralling around said longitudinal axis at least partially between the ends of the cutting head, said helical band defining a plurality of loops that are spaced from one another and being operable to allow said cutting head to flex relative to said longitudinal axis of said elongated shaft wherein said helical band allows said cutting head to flex with said opposed ends lying along relatively offset axes and allows said cutting head to remain along said relatively offset axes during rotation of said reamer.

15. The surgical reamer as set forth in claim 14, wherein said helical band has a helix angle of between about 60°–89° with respect to the longitudinal axis of said elongated shaft.

16. The surgical reamer as set forth in claim 14, wherein said helical band has a helix angle of about 84° with respect to the longitudinal axis of said elongated shaft.

17. The surgical reamer as set forth in claim 14, wherein said cutting head includes a plurality of cutting flutes that extend spirally along a portion of said cutting head.

18. The surgical reamer as set forth in claim 17, wherein the helix angle of successive flutes is between about 0°–45° with respect to the longitudinal axis of said cutting head.

19. The surgical reamer as set forth in claim 17, wherein said cutting head includes a plurality of helical flutes that extend spirally along a portion of said cutting head and the helix angle of successive flutes is about 15° with respect to the longitudinal axis of the cutting head.

20. A set of surgical instrumentalities for use in the replacement of a hip joint having a femur with a neck portion, said set of surgical instrumentalities comprising:
   a hip prosthesis including a distal segment and a proximal segment,
   a distal canal reamer operable to ream a diaphyseal cavity in the femur for receiving said distal segment of said hip prosthesis;

a proximal reamer operable to ream a metaphyseal cavity in the femur for receiving a portion of said proximal segment;

a femoral neck reamer operable to ream the neck portion of the femur for receiving a portion of said proximal segment, said femoral neck reamer having a shaft and a cylindrical longitudinally fluted cutting head having opposed ends, at least a portion of said cutting head being a helical band defining a plurality of cutting portions that are spaced from one another to enable said cutting head to flex relative to said shaft, said helical band allowing said cutting head to flex with said opposed ends lying along relatively offset axes and allowing said cutting head to remain along said relatively offset axes during rotation of said reamer; and a proximal reaming guide for positioning said neck reamer relative to the femur to ream said neck portion, said proximal reaming guide including a guide arm operable to guide said shaft of said femoral neck reamer.

21. The set of surgical instrumentalities as set forth in claim 20, wherein said proximal reaming guide comprises an axial guide body having a lower end portion adapted to be located in the metaphyseal cavity, a medial portion adapted to be located relative to the metaphyseal cavity, and an upper end portion which forms a handle to position said proximal reaming guide, and said guide arm extends medially from said upper end portion and forms generally a curved arc the center of which is generally located at said lower end portion.

22. The set of surgical instrumentalities as set forth in claim 21, wherein said guide arm has a bearing surface adapted to engage and guide said shaft of said femoral neck reamer for movement about the neck portion of the femur and to allow said femoral neck reamer to flex about the longitudinal axis of said shaft to enlarge the metaphyseal cavity of the femur.

23. The set of surgical instrumentalities as set forth in claim 22, further comprising a guide spool connected to said shaft of said femoral neck reamer, said guide spool being adapted to engage and maintain said shaft in an axially spaced relationship with respect to the metaphyseal cavity of the femur.

24. A set of surgical instrumentalities for replacing a hip joint having a femur in which a metaphyseal cavity has been formed, said set of surgical instrumentalities comprising a prosthetic device, a reamer adapted to extend into the metaphyseal cavity of a host femur, and a reaming guide for use with the reamer in preparing the metaphyseal cavity of the femur for said prosthetic device, said reamer comprising a hollow cutting head having at least one cutting flute and a shaft arranged coaxially along a longitudinal axis, the cutting head having a helical band spiralling between the opposing ends of said cutting head, wherein said helical band allows said cutting head to flex with said opposed ends lying along relatively offset axes and allows said cutting head to remain along said relatively offset axes during rotation of said reamer; and said reaming guide comprising an axial guide body having an upper end formed as a handle and a lower end supported in the femur, and a guide arm extending from the guide body, said guide arm having a bearing surface for engagement by said shaft of said reamer to guide said shaft when said cutting head is rotated in the metaphyseal cavity whereby to enlarge the metaphyseal cavity.

* * * * *

UNITED STATES PATENT AND TRADEMARK OFFICE
CERTIFICATE OF CORRECTION

PATENT NO. : 5,527,316
DATED : June 18, 1996
INVENTOR(S) : Stone et al.

It is certified that error appears in the above-identified patent and that said Letters Patent is hereby corrected as shown below:

Column 4, Line 20, insert "." after --axis--.

Column 4, Line 23, insert "." after --axis--.

Column 4, Line 29, "bit" should be --bite--.

Signed and Sealed this

Ninth Day of June, 1998

Attest:

BRUCE LEHMAN

Attesting Officer

Commissioner of Patents and Trademarks